United States Patent [19]

Parker

[11] 4,269,685
[45] May 26, 1981

[54] DISPOSABLE POLAROGRAPHIC GAS SENSOR SYSTEM

[75] Inventor: Dawood Parker, London, United Kingdom

[73] Assignee: McNeilabs, Inc., Fort Washington, Pa.

[21] Appl. No.: 85,186

[22] Filed: Oct. 16, 1979

[51] Int. Cl.$^3$ .............................................. G01N 27/54
[52] U.S. Cl. .................................................. 204/195 P
[58] Field of Search ........................... 204/195 P, 1 P; 128/635

[56] References Cited

U.S. PATENT DOCUMENTS

| 3,211,638 | 10/1965 | Halvorsen | 204/195 P |
| 3,666,650 | 5/1972 | Doniguian | 204/195 P |
| 4,172,770 | 10/1979 | Semersky et al. | 204/195 P X |

FOREIGN PATENT DOCUMENTS 1442303  7/1976  United Kingdom ................ 204/195 P

*Primary Examiner*—G. L. Kaplan
*Attorney, Agent, or Firm*—Audley A. Ciamporcero, Jr.

[57] ABSTRACT

A partially disposable, partially reusable polarographic sensor includes a fixed membrane and gel electrolyte in the disposable portion, and includes all electrical/metallic parts in the reusable portion. The disposable portion comprises a housing having a flow chamber for fluids to be monitored, adjacent to which is the membrane. Behind the membrane is the gel electrolyte, and a screw structure for engaging the reusable part. In turn, the reusable part employs a matable screw portion, and a fixed, coaxial anode-cathode assembly, which when mounted to the disposable portion, engages the membrane.

2 Claims, 5 Drawing Figures

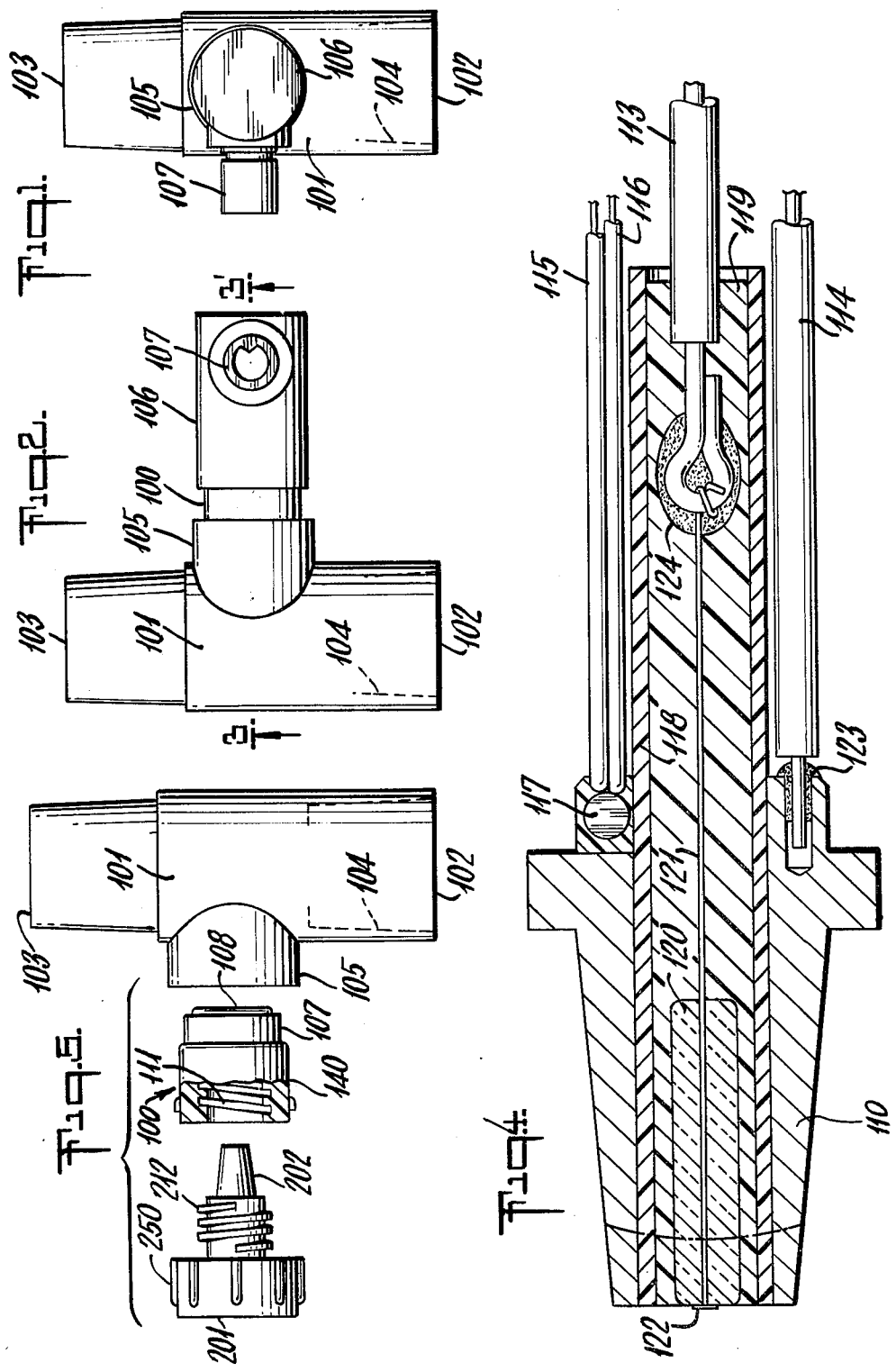

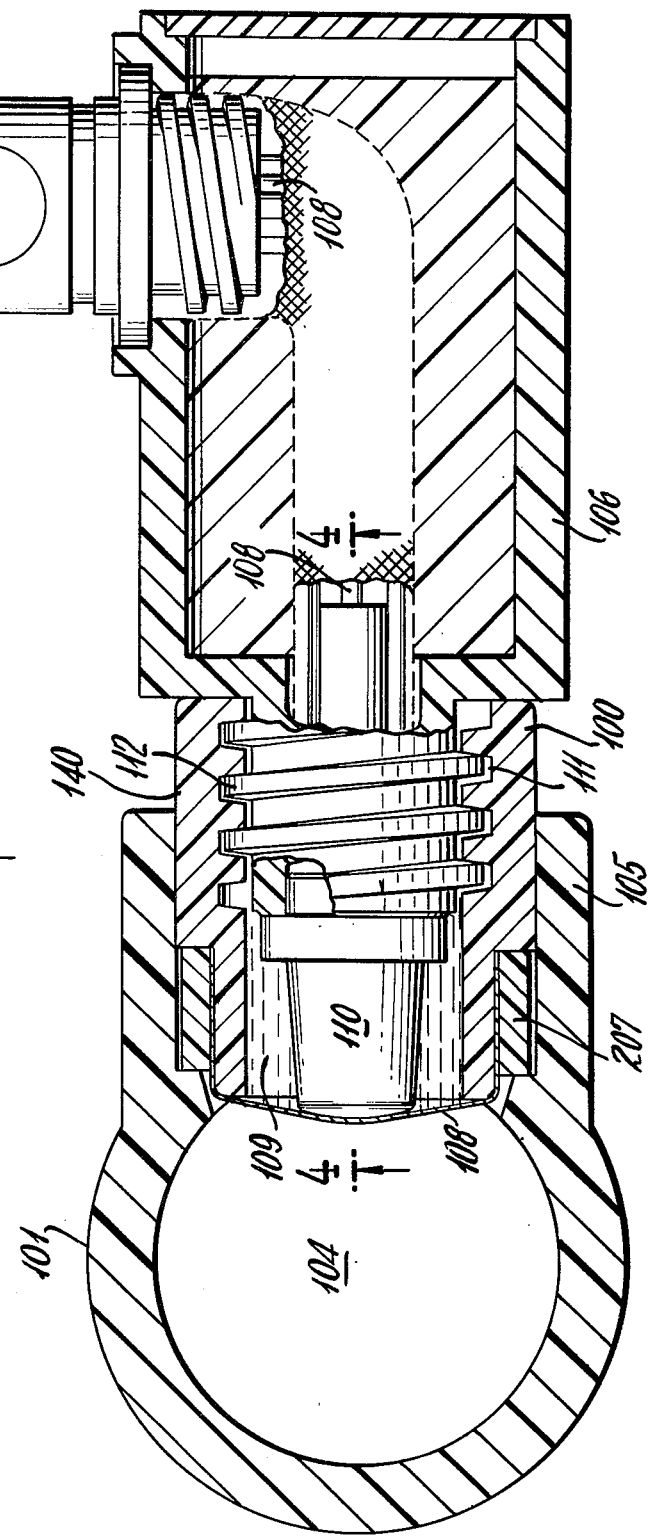

DISPOSABLE POLAROGRAPHIC GAS SENSOR SYSTEM

FIELD OF THE INVENTION

This invention relates to polarographic gas sensors, and more particularly to such sensors which are applicable to blood gas sensing and which include disposable portions.

BACKGROUND AND PRIOR ART

A class of electrochemical sensors known as polarographic sensors has become a popular approach to the measurement of gases in a sample medium, for example measuring partial pressures of oxygen, and the like in blood, or monitoring constituent gases being applied to the patient via an anesthesia circuit in the operating theatre. In accordance with these sensors, a cathode and an anode in contact with an electrolyte are arranged so that gases migrate across a selectively permeable membrane from the sample medium into the electrolyte of the cell. Potentials are set up whereby an electrode becomes polarized and thence is depolarized by ingress of the gas, enabling current to flow in the cell. Typically, the magnitude of the current flow is proportional to the partial pressure of the reactive gas, and thus the current flowing in the cell is a representation of the gas content.

Since the early description of such cells in U.S. Pat. No. 2,913,386 to L. C. Clark, it has been well understood by those of ordinary skill in the art that application of polarographic sensors to high precision applications, such as in the health care field, entails rigorous control of the physical configuration and dimensions of the components. For example, one chief drawback was found to be the difficulty in establishing and maintaining a stable, close spacing between the active surfaces of the electrodes and the inner surface of the selectively permeable membrane. The stability of the spacing determines the stability of the diffusion gradient of the gas through the membrane and electrolyte during sensor operation, and therefore in turn determines the proportional signal level for the gas partial pressure. Response time is also thereby affected. Likewise, it was determined early on that a fixed mechanical relationship between the anode and cathode are matters of considerable importance.

Hence, in the aggregate, polarographic sensors constitute a class of apparatus which is useful and valuable in fields including health care and critical care monitoring, but which generally has entailed rigorous maintenance of tolerance and configurational limitations. Also such sensors generally are difficult to fabricate on any high production basis.

U.S. Pat. No. 3,826,730 to H. Watanabe et al., entitled "DISPOSABLE ELECTROCHEMICAL ELECTRODE" and owned by the assignee hereof, represents a substantial step forward in the field of polarographic sensors. In accordance with the Watanabe et al. patent, an electrochemical sensor comprises a permanent electrode assembly and a replaceable or disposable electrode assembly, which can be easily attached together to form an electrochemical cell. The disposable assembly includes a selectively permeable membrane rigidly attached to the housing of the disposable portion, an electrolyte well or chamber also defined by the housing and communicating with the membrane, and a metallic button or wire which is affixed to the housing against the membrane to define the cathode electrode. Typically, the cathode button or wire is a noble metal such as silver, platinum, or gold. In accordance with the Watanabe et al. teachings, the sensors also include a reusable portion, including an anode electrode for insertion into the electrolyte well, a permanent cathode for connection in circuit relationship with the cathode button or wire, and suitable external cable connections.

The Watanabe et al. design, then, while proving relatively advantageous and economical relative to its predecessors, nevertheless involves some drawbacks. Principally, these relate to relative ease or difficulty of fabrication, and to the inclusion of valuable noble metal parts in the disposable portion of the device. That is, Watanabe et al. fix both the membrane and the cathode electrode in the disposable housing and in contact with one another, and provide an anode electrolyte well in the housing in predetermined relationship to the cathode and the membrane.

It is a primary object of the present invention to provide a partially reusable, partially disposable blood gas sensor which successfully utilizes polarographic principles, yet which has a relatively simple disposable structure, and which avoids the need to discard valuable noble metal components with the disposable portion. It is, accordingly, an associated object of the present invention to provide a partially reusable, partially disposable sensor wherein the reusable portion involves rigidly mounted anode and cathode assemblies, wherein the disposable portion includes membrane and electrolyte aspects, and wherein the joining of the reusable and disposable portions automatically meets all relevant tolerances with respect to electrode-membrane-electrolyte placements.

SUMMARY OF THE INVENTION

In accordance with the principles of the present invention, a partially reusable, partially disposable sensor includes a reusable portion including an anode-cathode polarographic assembly, preferably with the anode coaxially surrounding and holding the cathode. The disposable portion includes a housing defining a flow chamber for blood, adjacent to which a gas permeable membrane is fixedly mounted to the housing. A gelatinous electrolyte coats the opposite side of the membrane, so that when the disposable portion is coupled to the reusable portion, the cathode electrode contacts the membrane, and is isolated from the electrolyte by the coaxially surrounding anode. In turn, the anode itself is in continuous contact with the gelatinous electrolyte, thereby establishing a polarographic cell. In a preferred form, the disposable portion includes a disposable plug or blank, which mimics the form of the reusable portion, and which sealably occupies and defines space for the reusable portion to be mounted upon the disposable portion.

DESCRIPTION OF THE DRAWINGS

FIG. 1 shows a top view of a preferred embodiment of the present invention, including a reusable portion mounted fixedly into a disposable portion;

FIG. 2 shows a side view of the embodiment of FIG. 1;

FIG. 3 shows a partial cutaway of the embodiment of FIG. 2, illustrating mounting of the reusable portion, including an anode, within the gel and membrane assembly of the disposable portion;

FIG. 4 shows a partial cutaway of the FIG. 3 drawing, illustrating in detail the anode-cathode reusable assembly;

and FIG. 5 shows a composite, partially disassembled view of a disposable housing, a membrane-gel assembly for fixed, permanent mounting within the disposable housing, and a plug-blank for mounting in the membrane-gel portion and for disposal prior to use.

DESCRIPTION OF THE BEST MODE

Referring generally to FIGS. 1-4, there is shown a preferred embodiment of the principles of the present invention. In the figures, a housing 101 defines an input port 102, an output port 103, and a flow chamber 104 therebetween. Housing 101 defines an orthogonally directed protuberance 105, which is generally cylindrical in configuration. Rigidly and permanently mounted to the housing 101 at protuberance 105, and disposable therewith, is a cylindrical membrane-electrolyte assembly. Hence, the housing 101 including protuberance 105 and with membrane-electrolyte assembly 100 permanently mounted thereto, constitutes the disposable portion of a polarographic sensor embodying the principles of the present invention. A reusable portion 106 includes cable input connections 107, and an anode-cathode assembly removably mounted in the membrane-electrolyte assembly of the disposable portion.

Referring particularly to FIGS. 3 and 4, the detailed structural aspects of the principles of the present invention will be evident. In particular, in FIG. 3 the housing 101 is seen in cross-section to be circular, with the flow chamber 104 passing therethrough. Protuberance 105 extends outwardly from the chamber 104, so that when the membrane-electrolyte assembly 100 is permanently mounted within the protuberance 105, the membrane 108 is substantially adjacent the fluid flowing through the chamber 104.

As will be evident upon consideration of FIG. 5, the membrane-electrolyte assembly is preferably fabricated first and separately from the housing 101, and thereupon is rigidly and permanently mounted in protuberance 105 as shown in FIG. 3, prior to installation of the reusable assembly 106. The membrane-electrolyte assembly 100 comprises a housing portion 140 to which a membrane 108 is mounted by means of a snug, annular collar 207. The assembly 100 is shown to be mountable in close tolerance to the interior of cylindrical protuberance 105 and there joined, whereby assembly 100 and the housing 101 become a single, disposable unit. Also part of the single, disposable unit is a suitable amount of gelatinous electrolyte 109, which partially fills the recess within assembly 100 behind the membrane 108, and which upon entry of the reusable portion is moved out of the way to conform to the shape of the anode 110. The interior of the assembly 100 is provided with female threadings 111, which are adapted matably to engage corresponding male threaded portions 112 of the reusable electrode portion. Hence, the entire disposable assembly, including housing 101 and the membrane-electrolyte portion 100 may be mounted onto the reusable portion, thereby to comprise a complete electrochemical cell. The threads 111 and 112 are arrayed such that as the reusable portion is tightly engaged on to the disposable portion, the front end of anode 110 meets, engages, and slightly forwardly deforms the membrane 108, pushing the electrolyte gel away from that engagement and into surrounding relationship as shown in FIG. 3.

As noted in FIG. 4, a preferred construction for the reusable electrode portion in accordance with the principles of the present invention includes a frustoconical anode 110 which carries along its axis a wire 121, which at its tip 122 defines the effective cathode electrode. As may be most clearly seen from FIG. 4, the electrical aspects of the reusable portion include the anode 110 preferably composed of silver, a tubular epoxy support 118, a further epoxy potting 119 which encloses and holds the wire 121, and the glass tubing 120 which encloses wire 121. A solder joint 124, suitably enclosed by epoxy potting 119, establishes electrical connection between the cathode wire 121 and the exterior cathode cable 113. Likewise, a solder joint at 123 connects the anode 110 to the exterior anode cable connection 114. Advantageously, the reusable portion is provided with a thermistor 117 and its associated electrical connections 115 and 116. As is known in the art, polarographic cells are subject to variation in operation based on temperature conditions, and thermistor correction is provided in order accurately to interpret data generated by the electrochemical cell.

Referring again to FIG. 3, showing the exterior configuration of the anode 110, a threaded collar surrounds the distal portion of the FIG. 4 apparatus, providing insulation and providing proper engagement with the disposable portion of the electrochemical cell. The wire bundle 108, including anode cable 114, cathode cable 113, and thermistor cables 115 and 116, is enclosed and potted within a housing 106, and connects with receptacle 107. Preferably, receptacle 107 has conventional plug or clip connections for establishing an electrical circuit between the electrochemical cell of FIG. 3 and a utilization device such as appropriate signal processing and metering apparatus.

Referring generally to FIGS. 3 and 4, it will be noted that the effective area of the cathode electrode, when the reusable portion is installed within the disposable portion, is the cross section of cathode wire 121 which is exposed at point 122. As the reusable portion is installed against the membrane 108, area 122 is in direct contact with the membrane 108, and effectively is insulated from the anode by glass portion 120, epoxy sections 118 and 119, and the membrane 108 itself. Electrical characteristics and physical flow characteristics of the gelatinous electrolyte 109 prevent establishment of a short circuit connection between cathode 122 and anode 110. In turn, the anode 110 is enclosed by gelatinous electrolyte 109 and the membrane 108.

In a preferred embodiment, the housing 101 of the disposable portion, as well as members 140 and 207, are plastic materials which are electrically nonconductive and chemically nonreactive with the substances in question. Wire bundle 108 is potted within housing 106 by epoxy, advantageously the same epoxy 119 which is utilized to pot wire 121 within epoxy tube 118.

Referring to FIG. 5, there is shown a preferred approach to manufacture of the disposable portion, and shipment thereof for use with suitable reusable portions. In FIG. 5, the cylindrical housing 101 defines an input port 102, an output port 103, and an orthogonal, cylindrical protuberance 105. Preferably, the membrane-gel assembly 100 is separately fabricated, with cylindrical member 140 being formed with female threaded portions 111 on the inside thereof. Membrane 108 is stretched over the end of cylindrical member 140, and a ring or collar 207 is mounted to stretch the membrane 108 and hold it in place. The entire segment 110 is inserted and bonded into the cylindrical protuberance 105, either before or after a suitable amount of electrolyte gel material has been deposited within segment 100, adjacent to the membrane 108.

Also shown in FIG. 5 is a plug or blank 201, which mimics the shape of the reusable portion of the electrode. Specifically, plug 201 includes a frustoconical protuberance 202 and an adjacent threaded portion 212, both rigidly attached to a sealing knob area 250. The plug 201 preferably is screw inserted into the disposable portion for shipment, and prior to use of the disposable portion, the plug 201 is removed and discarded. Not only does the plug 201 provide protection for the membrane 108 and the gel material therein, but furthermore the utilization of a shape 202 and 212 similar to that of the reusable portion, arranges the gel in position easily to receive the reusable portion upon use.

The salient structural aspects of preferred embodiments of the present invention will therefore be appreciated from the foregoing. In a preferred embodiment adapted to monitor the partial pressure of oxygen in blood passing through chamber 104, the membrane 108 is low density polyethylene in the range of 10–15 μm. thick, coated on its inner surface (i.e. surface adjacent the gel electrolyte and reusable assembly) with a hydrophilic membrane material constituted from MeOH and commercially available under the trade name "pHEMA". The anode electrode 110 is silver, and the cathode wire 121 is platinum. The electrolyte 109 is a solution of propylene glycol and deionized water (50% each by volume), into which is added 0.6 molar potassium chloride. The electrolyte mix is made gelatinous by heating, the addition of commercially available gel agents known as agarose and CMC, and stirring to homogeniety.

Under conventional circumstances, it would be expected that when the disposable and reusable sections are connected together, the performance of the electrode would be critically dependent on the distribution of the electrolyte 109 within the electrode. For example, air bubbles or crevices in the electrolyte generally would cause the electrode to have a high zero current, i.e., high current in $N_2$, and be non-linear. The hydrophilic pHEMA membrane on the inside of the polyethylene membrane, however, forces oxygen trapped in bubbles in the electrolyte 109 to traverse a long diffusion path through the pHEMA membrane. Since the diffusion coefficient for oxygen is lower in pHEMA than in most conventional electrolytes, the effect of air bubbles on electrode performance is greatly diminished.

It will be appreciated by those of ordinary skill in the art that a variety of hydrophilic membrane materials can be so used as such a "back diffusion" barrier, although clearly the merits of such materials need to be assessed in terms of their other properties, for example gas permeability, temperature coefficient, ease of deposition, and the like.

It will be understood that the foregoing describes illustrative and preferred embodiments of the principles of the present invention, but that numerous alternative embodiments will occur to those of ordinary skill in the art without departure from the spirit and scope of the present invention.

What is claimed is:

1. A partially reusable, partially disposable blood gas sensor comprising:
   (a) a reusable portion including an anode-cathode polarographic assembly, and electrical connectors for establishing a circuit from said polarographic electrodes to an external utilization device;
   (b) a disposable portion including
      (i) a housing defining a blood input port, a blood output port, a flow chamber therebetween, and a gas sensing region contacting at least a portion of said chamber;
      (ii) a gas permeable membrane sealably overlying said gas sensing region for contact with blood in said chamber;
      (iii) a gelatinous electrolyte, responsive to said gas, coating the side of said membrane opposite said chamber; and
      (iv) means, integral with said housing, for removably coupling said reusable portion to said disposable portion, said means for coupling imbedding said polarographic assembly into said gelatinous electrolyte, wherein said means for removably coupling comprises a protuberance from said housing, surrounding said membrane and enclosing said gelatinous matter, said protuberance defining a threaded portion and said reusable portion defining a matably corresponding portion for screwed attachment of said reusable portion with said protuberance, simultaneously imbedding said assembly into electrolyte;
   (c) wherein said polarographic assembly comprises a frustoconical, hollow anode, carrying a cathode generally axially therein; and
   (d) disposable plug means, duplicating the shape of said reusable portion, and insertible into said protuberance of said disposable portion for storage and shipment prior to use.

2. In a blood gas sensor system having a reusable polarographic assembly including polarographic anode and cathode, a disposable sensor for repeatedly utilizing said assembly, comprising:
   (a) a housing defining a blood input port, a blood output port, a flow chamber therebetween, and a gas sensing region contacting at least a portion of said chamber;
   (b) a gas permeable membrane sealably overlying said gas sensing region for contact with blood in said chamber;
   (c) a gelatinous electrolyte, responsive to said gas, coating the side of said membrane opposite said chamber;
   (d) means, integral with said housing, for removably coupling said reusable portion to said disposable portion, said means for coupling imbedding said polarographic assembly into said gelatinous electrolyte with said anode and cathode being in direct contact with said membrane, wherein said means for removably coupling comprises a protuberance from said housing, surrounding said membrane and enclosing said gelatinous matter, said protuberance defining a threaded portion and said reusable portion defining a matably corresponding portion for screwed attachment of said reusable portion with said protuberance, simultaneously imbedding said assembly into electrolyte, and
   (e) disposable plug means, duplicating the shape of said reusable portion, and insertible into said protuberance of said disposable portion for storage and shipment prior to use.

* * * * *